(12) United States Patent
Kowaleski

(10) Patent No.: US 10,207,964 B2
(45) Date of Patent: Feb. 19, 2019

(54) PROCESS FOR MAKING CUMENE BY ALKYLATION OF BENZENE USING AN ORGANOTEMPLATE-FREE ZEOLITE BETA

(71) Applicant: SHELL OIL COMPANY, Houston, TX (US)

(72) Inventor: Ruth Mary Kowaleski, Cypress, TX (US)

(73) Assignee: SHELL OIL COMPANY, Houston, TX (US)

(*) Notice: Subject to any disclaimer, the term of this patent is extended or adjusted under 35 U.S.C. 154(b) by 0 days.

(21) Appl. No.: 15/284,945

(22) Filed: Oct. 4, 2016

(65) Prior Publication Data

US 2017/0096378 A1  Apr. 6, 2017

Related U.S. Application Data

(60) Provisional application No. 62/237,735, filed on Oct. 6, 2015.

(51) Int. Cl.
C07C 2/66 (2006.01)
C07C 6/04 (2006.01)
B01J 29/70 (2006.01)
C07C 15/085 (2006.01)

(52) U.S. Cl.
CPC ............. C07C 2/66 (2013.01); B01J 29/7007 (2013.01); C07C 6/04 (2013.01); C07C 15/085 (2013.01); C07C 2529/70 (2013.01)

(58) Field of Classification Search
CPC ...................................................... C07C 2/66
USPC ........................................................ 585/467
See application file for complete search history.

(56) References Cited

U.S. PATENT DOCUMENTS

| 3,308,069 | A | 3/1967 | Wadlinger et al. |
| 4,891,458 | A | 1/1990 | Innes et al. |
| 5,600,050 | A | 2/1997 | Huang et al. |
| 5,672,799 | A | 9/1997 | Perego et al. |
| 6,440,866 | B1 | 8/2002 | Collins et al. |
| 8,865,121 | B2 | 10/2014 | Xiao et al. |
| 2011/0286914 | A1 | 11/2011 | Li et al. |
| 2012/0259148 | A1 | 10/2012 | Yilmaz et al. |

Primary Examiner — Thuan D Dang
(74) Attorney, Agent, or Firm — Charles W. Stewart

(57) ABSTRACT

A process for making cumene by the alkylation of benzene with propylene using a benzene alkylation catalyst that comprises an organotemplate-free zeolite beta having a silica-to-alumina molar ratio of less than 20 and synthesized without an organic structure directing agent (SDA).

19 Claims, 1 Drawing Sheet

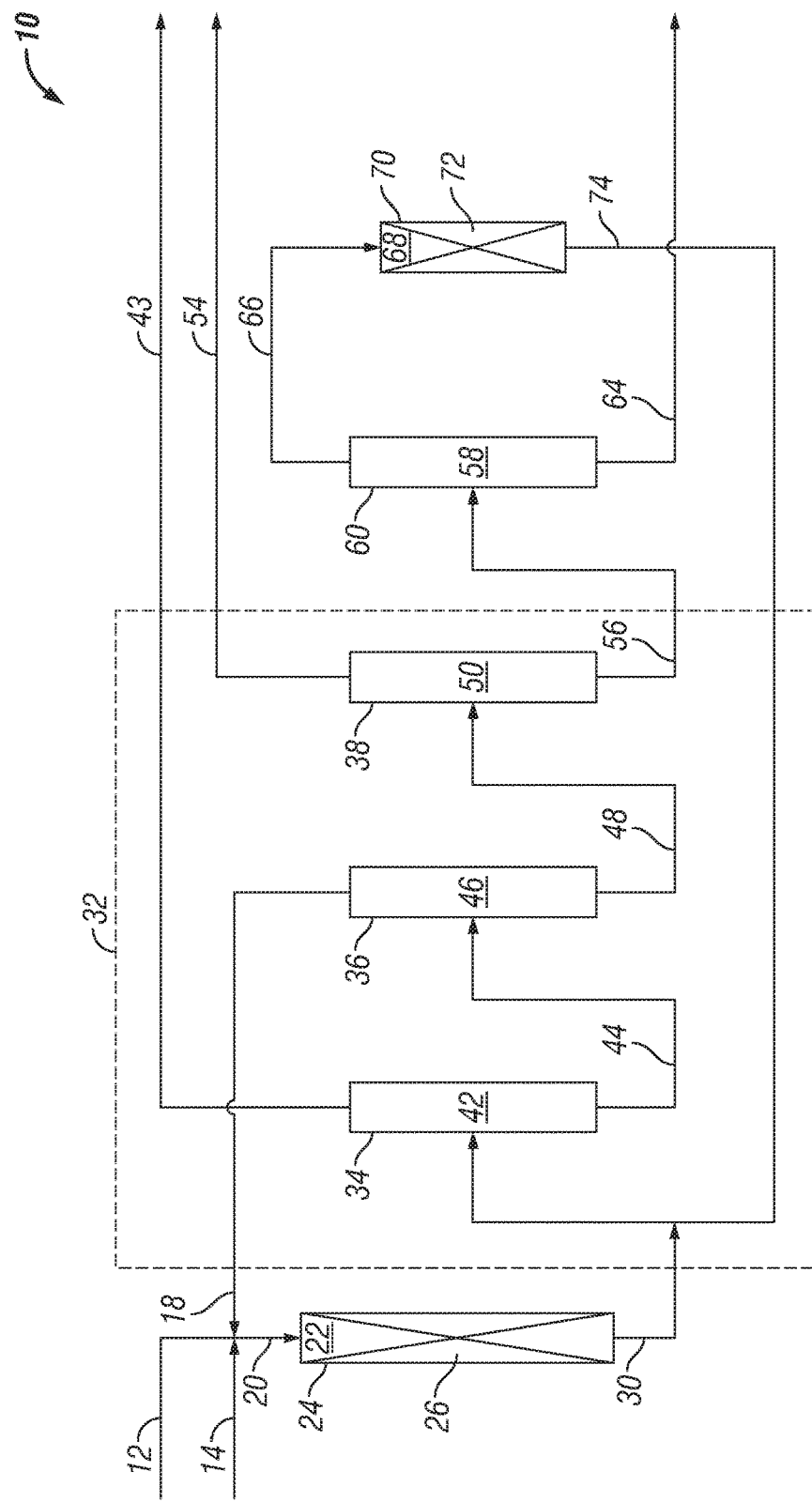

PROCESS FOR MAKING CUMENE BY ALKYLATION OF BENZENE USING AN ORGANOTEMPLATE-FREE ZEOLITE BETA

The present Non-Provisional Application claims priority from pending U.S. Provisional Application Serial No. 62/237,735 filed 6 Oct. 2015, the entire disclosure of which is incorporated herein by reference.

FIELD OF THE INVENTION

This invention relates to a process for making cumene by the catalytic alkylation of benzene with propylene using an alkylation catalyst comprising an organotemplate-free zeolite beta synthesized without the use of an organic structure directing agent.

BACKGROUND OF THE INVENTION

Zeolite beta has long been recognized as an aromatics alkylation catalyst. For instance, U.S. Pat. No. 4,891,458 discloses a process for alkylation of benzene with a C2 to C4 olefin using zeolite beta as a catalyst. The zeolite beta is the crystalline aluminosilicate originally described in U.S. Pat. No. 3,308,069. It is noted by the '458 patent that the zeolite beta should be predominantly in its hydrogen ion form in order to provide for high catalytic activity. The zeolite beta is converted to the hydrogen form by ammonium exchange followed by calcination. It is further preferred for the catalyst to be a shaped mixture of zeolite powder and an inorganic oxide binder.

U.S. Pat. No. 5,600,050 discloses the use of a modified zeolite beta as a catalyst that is used in the liquid phase alkylation of benzene to make cumene. The catalyst comprises from 30 to 70 wt. % H-beta zeolite with a silicon-to-aluminum ratio of from 20 to 40, from 0.5 to 10 wt. % of a halogen, and the balance being $\gamma$-$Al_2O_3$. The catalyst is prepared by converting a Na-beta zeolite to the H-form by ammonium exchange followed by calcination and then adding a halogen-containing compound to a mixture of the H-form beta zeolite and $\gamma$-$Al_2O_3$ precursor that is formed and calcined. It is claimed that the catalyst shows higher space-time yield and selectivity of cumene than prior art catalysts.

U.S. Pat. No. 5,672,799 teaches a process for the preparation of cumene by the alkylation of benzene with propylene using beta zeolite into which quantities of either alkaline, alkaline-earth or metallic cations have been introduced by means of ion exchange. It is asserted that the catalyst system has good activity and selectivity to cumene of the converted benzene which is higher than provided by zeolite beta that is either partially or totally in the acid form. The zeolite beta is prepared as described in U.S. Pat. No. 3,308,069 followed by its conversion to the acid form by ammonium treatment and calcination and then ion exchanged with an ion selected from $Na^+$, $K^+$, $Ca^{2+}$ or $Ni^{2+}$. The zeolite may be mixed with a binder in relative quantities of between 50:50 and 95:5.

Disclosed in U.S. Pat. No. 6,440,886 is a modified zeolite beta catalyst that is active in the alkylation of aromatics with olefin and exhibits a lower deactivation rate for a given temperature than conventional zeolite beta. The catalyst comprises a calcined, non-template surface-modified zeolite beta. To make the catalyst, an as-synthesized and templated zeolite beta is acid washed with a strong acid followed by removal of the template by calcination.

An organotemplate-free synthesis process for making zeolite beta is described in U.S. Pat. No. 8,865,121. The zeolitic materials having a BEA framework structure made by the organotemplate-free synthesis process are considered to be novel having unique properties. The process yields a zeolite with a BEA framework structure that is enriched with respect to a particular polymorph compared to the products of a BEA framework structure made by synthesis methods that use an organotemplate. The X-ray powder diffraction pattern of the beta zeolitic material of the organotemplate-free synthesis process exhibit reflections that are shifted in their 2° Theta values compared to the X-ray powder diffraction pattern of beta zeolitic material made by an organotemplate-mediated synthesis process.

U.S. Publication 20120259148 discloses an alkylation process that uses a catalyst comprising a zeolite beta obtained from a synthesis process that does not use an organotemplate as the structure directing agent. The alkylation process is broadly described as reacting an alkylatable organic compound with an alkylating agent to obtain an alkylated organic compound. However, only the two alkylation reactions of benzene with ethene and toluene with ethene are presented in the examples.

There is an ongoing desire to develop improved processes for the alkylation of benzene with propylene to make cumene. It is desirable for such processes to provide for high cumene selectivity even with reduced or low alkylation reactor inlet temperatures, high weight hourly space velocities, and reduced feed benzene-to-propylene molar ratios. Due to the unique properties of zeolite beta made by an organotemplate-free synthesis process and other of its beneficial features, it is a further object of the invention to use such a zeolite beta product as a catalyst in the production of cumene.

BRIEF SUMMARY OF THE INVENTION

Accordingly, provided is process for preparing cumene by alkylation of benzene with propylene. This process comprises contacting a feed mixture, comprising benzene and propylene, at a reduced reactor inlet temperature and an elevated WHSV, with a benzene alkylation catalyst. The benzene alkylation catalyst is contained within a reaction zone defined by a reactor, wherein the benzene alkylation catalyst comprises an organotemplate-free zeolite beta, having a silica-to-alumina molar ratio (SAR) of less than 20, that is synthesized in the presence of a material absence of an organotemplate. An alkylation product, comprising cumene, is yielded from the reaction zone of the reactor.

BRIEF DESCRIPTION OF THE DRAWING

FIG. 1 is a process flow schematic of an embodiment of the inventive process for making cumene by catalytic alkylation of benzene with propylene by using an alkylation catalyst comprising an organotemplate-free zeolite beta providing for enhanced cumene selectivity and process operation.

DETAILED DESCRIPTION OF THE INVENTION

It has surprisingly been found that the cumene selectivity of a process for propylene alkylation of benzene to make cumene is materially improved by the use of a benzene alkylation catalyst comprising an organotemplate-free zeolite beta having a silica-to-alumina molar ratio of less than 20 and synthesized without the use of an organic structure directing agent as opposed to the use of a catalyst comprising zeolite beta made using an organic structure directing agent.

These unique properties of the organotemplate-free zeolite beta can be exploited to provide the improved and inventive process for making cumene. Embodiments of the inventive process are capable of operating with relatively low feed benzene-to-propylene molar ratios and low benzene recycle rates compared to prior art processes while still achieving improved cumene selectivity. The energy requirements of the inventive process are significantly lower than prior art processes because of its reduced feed benzene-to-propylene molar ratio, higher weight hourly space velocity, and lower benzene recycle rate.

The zeolite beta of the benzene alkylation catalyst is referred to herein as an organotemplate-free zeolite beta; because, it is made or synthesized from a crystallization mixture that contains no organic structure directing agent. As the term organotemplate-free zeolite beta is used in this specification, it does not encompass zeolite beta materials that are made using conventional methods which include the use of an organic structuring agent in their preparation but which have been calcined or otherwise treated in a manner so as to remove remnants of the organic structuring agent from the recovered zeolite beta material. Thus, the term also excludes recovered zeolites prepared using an organic template that are calcined to remove remnants of the organic template.

The use of an organotemplate-free beta instead of a zeolite beta that is conventionally prepared using an organic template is an essential feature of the inventive process for making cumene by the propylene alkylation of benzene. Examples of organic templates known in the art for making zeolite beta include the tetraethyl ammonium cation, tetraalkylammonium, dibenzylmethylammonium salts, and dibenzyl-1,4-diazabicyclo[2,2,2] octane. None of these templates are to be used in the preparation of the organotemplate-free zeolite beta component of the benzene alkylation catalyst of the inventive process.

The organic template-free zeolite synthesis process and the zeolites produced by the process are described in several patent publications. The recently granted U.S. Pat. No. 8,865,121 describes an organotemplate-free zeolitic material having a BEA framework structure that is prepared using a synthesis or crystallization mixture that is free of or has a material absence of or contains nor more than an impurity of an organic structure directing agent. The beta zeolite prepared by the organotemplate-free process of U.S. Pat. No. 8,865,121 exhibits novel properties and is enriched with respect to a certain polymorph as compared to zeolite beta made from crystallization mixtures using an organotemplate. U.S. Pat. No. 8,865,121 with its descriptions of the organotemplate-free zeolite beta and its preparation are incorporated herein by reference.

U.S. Publication 20110286914 is another patent publication that describes a method of making zeolite beta from a synthesis solution that is free of an organic structure directing agent (SDA). The synthesis solution disclosed in this publication includes a mixture of an aqueous solution of NaOH, a source of alumina, a source of silica, and a source of zeolite beta seed crystals in proportions such that the synthesis solution has the following mole ratio of raw materials: $SiO_2/Al_2O_3$=15-45, $Na_2O/SiO_2$=0.20-0.50, $H_2O/SiO_2$=4-50.

Zeolite crystal seed is added and the mixture is allowed to crystallize at elevated temperature to obtain zeolite beta crystals having a silica to alumina molar ratio (SAR) of from 5 to 15. Preferably, the mixture is allowed to crystallize at a temperature of from 100 to 180° C. for 12 to 24 hours. The molar composition is adjusted as is necessary to provide the organotemplate-free zeolite beta having the required silica-to-alumina ratio of the inventive benzene alkylation process for making cumene. The silica-to-alumina ratio of the organotemplate-free zeolite beta of the inventive process is discussed elsewhere herein. U.S. Publication 20110286914 and the descriptions of its process for producing beta zeolite without using an organic structure directing agent (SDA) and the zeolite beta made by the process are incorporated herein by reference.

Examples of possible sources of alumina include sodium aluminate, aluminum hydroxide, alumina, aluminum nitrate, and aluminum sulfate.

Examples of possible sources of silica include silica gel or silica sol. Other sources of silica include silicates, sodium silicate, sodium metasilicate, colloidal silica, precipitated silica, and silica-alumina.

The zeolite beta seed crystals may be from any source including zeolite beta that is made by conventional methods that use an organic template in its manufacture. Generally, the amount of seed crystals contained in the synthesis mixture is in the range of from 0.1 to 50 wt. % of the $SiO_2$ component.

The crystallization is conducted in a single vessel that is equipped with means for stirring the mixture while heating it at a crystallization temperature in the range of from 80 to 200° C., preferably, from 90 to 180° C., and more preferably from 95 to 170° C. The crystallization is conducted under autogenous pressure, which is typically in the range of from 13 psi to 220 psi.

The duration of the crystallization is typically for a period in the range of from 2 hours to 100 hours, but, preferably, from 8 to 70 hours.

The crystallization product is recovered from the synthesis solution by any suitable means or method for recovering crystallized zeolite beta. Examples of such means or methods include filtration, ultrafiltration, centrifugation and decantation. The recovered product may then be washed with a suitable solvent or washing agent such as water, an alcohol (methanol, ethanol or propanol) and mixtures thereof. The washed product can then be dried using any known method or it can be mixed with water to form a slurry and spray dried. The drying can be conducted at a drying temperature in the range of from 25° C. to 150° C.

The recovered zeolite beta product of the invention is an organotemplate-free zeolite beta made without the use of an organic structure directing agent. It is an essential feature of the inventive process for the organotemplate-free zeolite beta to have a relatively low silica-to-alumina molar ratio (SAR). Hence, the composition of the synthesis solution must be controlled in a manner to provide the organotemplate-free zeolite beta product having the necessary SAR.

It, thus, is critical for the SAR of the organotemplate-free zeolite beta of the inventive process to be less than 20. It is preferred for the SAR of the organotemplate-free zeolite beta to be less than 18, more preferably, the SAR is less than 15, and, most preferably, the SAR is less than 12. The lower limit of the SAR of the organotemplate-free zeolite beta typically is greater than 1, and, more typically, the SAR is greater than 3, or greater than 5.

The recovered zeolite beta can be further characterized as having a volume average crystal size as determined by scanning electron microscopy of from 10 to 1000 nanometers, and, more typically, from 50 to 500 nanometers.

Its surface area is typically from 400 to 800 m²/gram, more typically, from 550 to 750 m²/gram, as measured by the B.E.T. method according to ASTM test D3663-03.

The micropore volume preferably is of from 0.10 to 0.40 cc/gram, more specifically of from 0.15 to 0.3 cc/gram, as determined by ASTM test D4365-95.

A further important feature of the zeolite beta is for it to have a material absence of or to be free of a metal component selected from the group of metals consisting of copper (Cu), iron (Fe), cobalt (Co), chromium (Cr), nickel (Ni), vanadium (V), and niobium (Nb), and, especially, that the zeolite beta has a material absence of, or is free of, Cu or Fe, or both metals as a component. What is meant by having a material absence of the metal component is that its concentration in the zeolite beta is such that it does not affect performance of the zeolite beta as a benzene alkylation catalyst.

It is noted that metal-containing zeolite beta described and claimed in U.S. Publication 20110286914, due to its metal component, is not a suitable zeolite for use as a benzene alkylation catalyst of the inventive process. The zeolite beta that is derived from the organotemplate-free synthesis method is described in U.S. Publication 20110286914, without the further introduction of a metal component (e.g., Cu and Fe) into the zeolite beta product, can, however, be used as an acceptable benzene alkylation catalyst of the inventive process.

The benzene alkylation catalyst of the inventive process comprises the organotemplate-free zeolite beta described above. This zeolite beta material may be used alone, without either active or inactive additional components, as the benzene alkylation catalyst, or it may be a component within a shaped or formed composition or mixture of components that includes the zeolite beta.

One suitable benzene alkylation catalyst of the invention comprises a mixture of a binder material (e.g. an inorganic oxide) and the organotemplate-free zeolite beta. When the organotemplate-free zeolite beta is combined with a binder material and shaped or formed into a catalyst particle to provide a benzene alkylation catalyst, it generally can comprise relative amounts of the zeolite beta and binder material in the range of from 1:100 to 80:20 (weight parts binder-to-weight parts zeolite). It is preferred for the weight ratio of zeolite beta to binder material to be in the range of from 5:95 to 60:40, and, more preferred, the weight ratio is in the range of from 10:90 to 40:60.

The binder material can be selected from the group of inorganic binders such as silica, alumina, silica-alumina, titania, zirconia, ceria and gallia. The preferred binder is either alumina or silica, but alumina is the most preferred binder material.

In the present invention, the alumina to be used as inorganic binder may originate from any source. Preferably, the binder is boehmite such as Catapal or Pural available from Sasol. The benzene alkylation catalyst particles are typically formed by mixing the organotemplate-free zeolite beta, which is typically in powder form, with the binder material which also is typically is in powder form, with water, and, if desired or necessary, a chemical aid such as a peptizing agent, flocculating agent, or other compound to assist in forming a mixture or paste that may be formed into an agglomerate or shaped particle.

In one preferred method, the mixture of organotemplate-free zeolite beta and binder material is extruded to form extrudates of any one or more various shapes such as cylinders and trilobes having nominal sizes such as ¹⁄₁₆ inch, ⅛ inch and ³⁄₁₆ inch.

The agglomerates or shaped particles can be dried under standard drying conditions that can include a drying temperature in the range of from 50 to 200° C., preferably, from 90 to 150° C.

After drying, the shaped and dried particles can be calcined under standard calcination conditions that include a calcination temperature in the range of from 250 to 900° C., preferably, from 300 to 800° C., and, most preferably, from 350 to 600° C.

It is an unexpected aspect of the inventive process that the use of the benzene alkylation catalyst, comprising a low-SAR, organotemplate-free zeolite beta, in the propylene alkylation of benzene provides for an enhanced cumene selectivity when compared with such processes that use benzene alkylation catalyst compositions comprising zeolite beta synthesized using a conventional structure directing agent. Additionally, with its use of the low-SAR, organotemplate-free zeolite beta benzene alkylation catalyst the inventive process unexpectedly provides a high cumene selectivity even under benzene alkylation reaction conditions that include reduced or low alkylation reactor inlet temperatures, high feed WHSVs and reduced or low feed benzene-to-propylene molar ratios.

An embodiment of the inventive benzene alkylation process includes contacting a feed mixture, comprising benzene and propylene, with the benzene alkylation catalyst of the invention, which comprises a low-SAR, organotemplate-free zeolite beta, under the benzene alkylation reaction conditions of the inventive process and yielding an alkylation product, comprising cumene. It is unexpected that this process provides for high cumene selectivity and propylene conversion even when the benzene alkylation reaction conditions include charging the alkylation reactor of the process with a feed mixture at a rate such that the WHSV is elevated, or at a reduced inlet temperature, or with a reduced benzene-to-propylene molar ratio. There are number of economic benefits from operating a benzene alkylation process for making cumene at the aforementioned reaction conditions.

As noted above, the feed mixture charged to the alkylation reactor of the inventive process may be significantly reduced while still maintaining a higher cumene selectivity than with comparative processes. The alkylation reactor can be any reactor vessel or system known to those skilled in the art defining an alkylation reaction zone, containing an alkylation catalyst, and providing means for contacting the feed mixture with the alkylation catalyst under alkylation reaction conditions. The feed mixture is charged to the inlet of the alkylation reactor at a reduced temperature.

It is recognized that the reactor inlet temperature of the feed mixture of the process may be controlled by adjusting the benzene recycle rate in response to differences in the reactor inlet temperature of the feed mixture so as to provide a desired reactor inlet temperature of the feed mixture. An additional feature of the inventive alkylation process is that the feed mixture has a benzene-to-propylene molar ratio that is significantly reduced while still maintaining a higher cumene selectivity than comparative processes which utilize conventional alkylation catalysts.

The inventive process includes charging to a benzene alkylation reactor, which defines a benzene reaction zone containing the low-SAR, organotemplate-free zeolite beta, a feed mixture that comprises benzene and propylene. The feed mixture typically has a stoichiometric excess of benzene relative to propylene with the benzene-to-propylene molar ratio (B/P ratio) in the range upwardly to 12:1. High B/P ratios tend to favor cumene selectivity and prevent fouling and deactivation, but the higher ratios also require higher recycle rates of the unreacted benzene. Hence, the economics of the process as well as the catalyst can limit the operating B/P ratio.

It is desirable to be able to operate the process at as low of a B/P ratio as is feasible without resulting in fouling of the catalyst leading to lower selectivity and deactivation. This is one of the advantages of the inventive process in that it allows for its operation at a reduced B/P ratio while still providing for a high cumene selectivity and propylene conversion. Therefore, the B/P ratio of the feed mixture contacted with the low-SAR, organotemplate-free zeolite beta preferably is in the range of from 1:1 to 9:1, but it is best when the upper limit of the B/P ratio is less than 8:1 and even less than 7:1. Practically, the lower limit for the B/P ratio is greater than 2:1, or even greater than 3:1. A particularly preferred B/P ratio is in the range of from 3:1 to 7:1. As has been noted, there are benefits to charging the benzene alkylation reactor with a feed mixture at a reduced temperature while still providing for a high cumene selectivity and propylene conversion. The inventive process, with its use of the low-SAR, organotemplate-free zeolite beta, provides for a relatively lower benzene alkylation reactor inlet temperature than comparative processes while still maintaining high cumene selectivity and essentially 100% propylene conversion. This reduced reactor inlet temperature is generally less than 160° C., but it is preferred to be less than 145° C., and, more preferred, the reactor inlet temperature is less than 135° C. The lower limit for the reactor inlet temperature is greater than 80° C. or 90° C. It is most preferred for the reactor inlet temperature to be less than 130° C., such as, in the range of from 80° C. to 130° C. It is understood that the alkylation reaction is exothermic and that the temperature across the catalyst bed of the reactor will have a gradient due to the heat released by the alkylation reaction.

The WHSV of the inventive process is relatively high, which means that the feed mixture is in contact with the low-SAR, organotemplate-free zeolite beta for a shorter time than with a lower WHSV. The inventive process can operate with a WHSV greater than 6 $hr^{-1}$ and still provide for a high cumene selectivity and near complete propylene conversion. It is preferred for the WHSV to be as high as feasible while still achieving near complete (i.e., 100%) conversion of the propylene.

Thus, the WHSV of the inventive process can be greater than 7 $hr^{-1}$, preferably, greater than 8 $hr^{-1}$, and, more preferably, greater than 10 $hr^{-1}$. An upper limit for the WHSV of the inventive process can be less than 25 $hr^{-1}$ or less than 20 $hr^{-1}$. Even with the process operating at these high space velocities it still is able to provide acceptably high cumene selectivity and propylene conversion.

It is desirable to conduct the reactions of the inventive process in the liquid phase or at least in a partial liquid phase. Thus, the reaction pressure is such as to maintain the feed mixture during the reaction at least partially in the liquid phase or in a total liquid phase. The reaction pressure, therefore, typically is in the range of from 15 to 45 bar, preferably, it is in the range of from 18 to 35 bar.

As noted above, one of the surprising aspects of the inventive process is that it provides for an exceptional cumene reaction selectivity. The cumene selectivity is defined herein to be the moles of cumene that is yielded by the benzene alkylation reaction (i.e., moles of cumene leaving the benzene reaction zone less moles of cumene entering the benzene reaction zone) divided by the sum of all other products, which may include di- and tri-isopropylbenzenes, n-propylbenzene, alpha-methylstyrene, cymene, other aromatic products, and C6, C9, C12, and C15 oligomers.

The inventive process provides for a high cumene selectivity that is generally at least 94% even with its operation being under mild benzene alkylation reaction conditions. It is preferred for the cumene selectivity of the process to be at least 94.5%, but it is more preferred for it to be at least 95%. A most preferred cumene selectivity exceeds 95.2%.

The alkylation product yielded from the alkylation reaction step of the inventive process includes reaction products and unreacted benzene. The reaction product comprises cumene and smaller amounts of other reaction products including, di- and tri-isopropylbenzene. The reactor effluent may also contain inert propane which is introduced with the propylene feed.

In an embodiment of the inventive process, an alkylation product is passed to a separation system that provides for separating the alkylation product to yield a propane product stream, a benzene product stream, and a poly alkylated benzene product stream. An unexpected feature of the inventive process is that it requires a lower benzene recycle rate due to the lower required feed molar ratios of benzene-to-propylene than prior art processes require because of the much higher cumene selectivity of organotemplate-free zeolite beta alkylation catalyst of the inventive process. The benzene product stream provided by the separation system is, thus, recycled as a feed to the alkylation reactor by mixing a portion of the benzene product stream with the feed mixture charged to the alkylation reactor.

The poly alkylated benzene product stream is passed to a separation system providing means for separating diisopropylbenzene from the poly alkylated benzene product stream to yield a diisopropylbenzene product stream and a heavy hydrocarbon stream.

To provide further conversion of the diisopropylbenzenes, the diisopropylbenzene product stream is passed to a transalkylation reactor that defines a transalkylation reaction zone containing a transalkylation catalyst. The diisopropylbenzene product stream is contacted with the transalkylation catalyst under transalkylation reaction conditions to yield a transalkylation reaction product. At least a portion of the transalkylation reaction product is passed or mixed with the alkylation product that is passed to the separation system.

The transalkylation catalyst of the transalkylation reaction zone may be any suitable transalkylation catalyst known to those skilled in the art and which provides for the transalkylation of the diisopropylbenzene product stream to yield a transalkylation reaction product.

Suitable transalkylation catalysts typically are zeolite-based which include one or more zeolites having a framework structure, such as, for example, ZSM-5, ZSM-11, ZSM-12, ZSM-23, zeolite beta, MCM-22, faujasite, or mordenite. The transalkylation catalyst, in addition to the zeolite component, may further include an inorganic oxide component, such as alumina, as a binder material. The transalkylation catalyst further may include a metal catalytic component, such as a noble metal, for example, platinum or palladium, or another metal that may include molybdenum or nickel.

Reference is now made to FIG. 1 which presents a process flow schematic of an embodiment of the inventive cumene manufacturing process 10. Cumene manufacturing process 10 provides means for making cumene by catalytic alkylation of benzene with propylene using an alkylation catalyst comprising an organotemplate-free zeolite beta and the separation of the reaction products.

Make-up benzene passing by way of line 12 and propylene passing by way of line 14 are combined with recycle benzene passing through line 18 to form a feed mixture comprising benzene and propylene in certain required proportions. The preferred relative proportions of benzene and propylene are such that the molar ratio of benzene-to-propylene of the feed mixture less than 12:1.

The feed mixture passes through line 20 and is introduced into benzene alkylation zone 22 which is defined by benzene alkylation reactor 24 that contains benzene alkylation catalyst 26. Benzene alkylation catalyst 26 provides for a high cumene selectivity under specifically defined benzene alkylation conditions and comprises an organotemplate-free zeolite beta having a silica-to-alumina molar ratio of less than 20:1.

The feed mixture is contacted with benzene alkylation catalyst 26 within benzene alkylation zone 22 under the specified benzene alkylation conditions. It is a feature of the inventive cumene manufacturing process 10 that the benzene alkylation reaction conditions may include such process parameters as a high WHSV, a low reaction temperature, and a low feed molar ratio of benzene-to-propylene. These reaction conditions provide numerous benefits and advantages, including a significantly more energy efficient process, and they provide for lower process equipment costs.

An alkylation product that comprises unreacted benzene, cumene and other reaction products, such as propane, poly alkylated benzenes, and heavier by-products, is yielded and passes from benzene alkylation zone 22 through line 30 to separation system 32. Separation system 32 includes depropanizer column 34, benzene recycle column 36 and cumene column 38 that are arranged in series flow.

The alkylation product passes by way of line 30 and is introduced into propane fractionation zone 42 defined by depropanizer column 34. Depropanizer column 34 is any suitable fractionation system known to those skilled in the art which defines propane fractionation zone 42 and provides means for separating propane from the alkylation product to yield a propane product stream, comprising propane, and a propane column bottoms stream, comprising benzene, poly alkylated benzenes and other reaction products. Propane product stream passes from propane fractionation zone 42 by way of line 43 to downstream.

The propane column bottoms stream passes through line 44 and is introduced into benzene fractionation zone 46 defined by benzene recycle column 36. Benzene recycle column 36 is any suitable fractionation system known to those skilled in the art which defines a benzene fraction zone 46 and provides means for separating benzene from the propane column bottoms stream to yield a benzene product stream, comprising benzene, and a benzene bottoms product stream, comprising poly alkylated benzene compounds and other reaction products.

At least a portion and, preferably, a major portion of the benzene product stream is recycled for use as a component of the feed mixture charged to benzene alkylation zone 22. A feature of inventive cumene manufacturing process 10 is that its required feed benzene-to-propylene molar ratio is much reduced while cumene manufacturing process 10 still provides for a very high cumene selectivity. This much reduced benzene-to-propylene molar ratio requirement provides for a lower required benzene recycle rate and lower energy requirements associated with the separation steps of cumene manufacturing process 10. The higher WHSV of the process allows for the use of a smaller benzene alkylation reactor 24 and a smaller volume of benzene alkylation catalyst 26 while still providing for a very high cumene selectivity.

Thus, at least a portion of the benzene product stream passes from benzene fractionation zone 46 by way of line 18 and is mixed or otherwise charged with the feed mixture into alkylation reaction zone 22 wherein it is contacted as a part of the feed mixture with benzene alkylation catalyst 26.

The benzene bottoms product stream passes through line 48 and is introduced into cumene fractionation zone 50 defined by cumene fractionation column 38. Cumene fractionation column 38 is any suitable fractionation system known to those skilled in the art which defines a cumene fractionation zone 50 and provides means for separating cumene from the benzene bottoms product stream to yield a cumene product stream, comprising cumene, and a poly alkylated benzene product stream. The cumene product stream passes from cumene fractionation zone 50 through line 54.

The poly alkylated benzene product stream passes from cumene fractionation zone 50 through line 56 and is introduced into or charged to polyisopropylbenzene fractionation zone 58 defined by polyisopropylbenzene column 60. Polyisopropylbenzene column 60 is any suitable fractionation system known to those skilled in the art which defines a polyisopropylbenzene fractionation zone 58 and provides means for separating polyisopropylbenzene from a heavies product stream, comprising heavy alkylation reaction by-products, to yield a diisopropylbenzene product stream, comprising diisopropylbenzene, and the heavies product stream. The heavies product stream passes from polyisopropylbenzene fractionation zone 58 through line 64.

The diisopropylbenzene product stream passes from polyisopropylbenzene fractionation zone 58 through line 66 and is introduced into transalkylation reaction zone 68 which is defined by transalkylation reactor 70 that contains transalkylation catalyst 72. The diisopropylbenzene product stream is contacted with transalkylation catalyst 68 within transalkylation reaction alkylation zone 68 under suitable transalkylation conditions. A transalkylation product is yielded and passes from transalkylation zone 68 passes through line 74 to be charged or introduced into propane fractionation zone 42 either with the alkylation product or as a separate feed.

The following Example is presented to illustrate the invention but it should not be construed as limiting the scope of the invention.

EXAMPLE

This Example presents the performance data for two different zeolite beta-based benzene alkylation catalysts used in benzene alkylation reactions to make cumene. One of catalysts contain a zeolite beta that is conventionally prepared and the other contains is an organotemplate-free beta.

Catalyst A is an extrudate catalyst made from of 20% alumina binder and 80% of a standard zeolite beta that is commercially available and conventionally manufactured by the use of an organic structure directing agent. The silica-to-alumina ratio of the zeolite beta was 23.

Catalyst B is an extrudate made using 20% alumina binder and 80% of an organotemplate-free zeolite beta synthesized without the use of an organic structure directing agent. The zeolite beta was synthesized by a method similar to the organotemplate-free beta synthesis described in Example 1 of U.S. Publication 2011/0286914. The silica-to-alumina ratio of organotemplate-free synthesized beta was 10.

The zeolite beta obtained from the organotemplate-free synthesis was mixed with alumina binder (Pural SB1) in a weight ratio of 80:20 with 0.5% wt. Superfloc 16 and water. The mixture had a loss on ignition of 40.5%. This mixture was extruded to obtain 1.6 mm diameter extrudates, dried for 12 hours at 120° C. and calcined for 4 hours at 550° C. No metal was incorporated into the synthesized zeolite beta.

Catalysts were tested in a ⅝" I.D. stainless steel reactor tube containing 12.0 g of catalyst (as 1/16" extrudate) mixed with 70 mesh silicon carbide. The reactor tube with catalyst was heated in a 5-zone furnace to 130° C. while flowing nitrogen from the bottom at 150 SCCM for 16 hours. The reactor pressure was increased to 300 psig with nitrogen, and then benzene was pumped into the bottom of the reactor at the desired rate. When the reactor tube was full with benzene, propylene was introduced by using an ISCO piston pump followed by a mass flow controller. Liquid samples are taken every 3-5 hours and analyzed by GC. Head space samples were taken periodically to verify the absence of propylene in the product gas phase.

Table 1 presents the test results from using each of the catalysts in benzene alkylation to yield cumene at three different reaction temperatures. In these tests, each catalyst was tested for its performance in the propylene alkylation of benzene. A feedstock comprising benzene and propylene at relative amounts so as to provide a benzene-to-propylene molar ratio of 7.6 was passed over the catalyst in a reactor maintained at different reaction temperatures and at a rate so as to provide a weighted hourly space velocity (based on total benzene and propylene) of 6 $hr^{-1}$. The WHSV based on propylene flow was 0.42 $hr^{-1}$. The reaction pressure was 300 psig (21.7 bar). The reactor temperatures are presented in the tables.

The data presented in Table 1 show that for all temperatures Catalyst B provides a higher cumene selectivity. Thus, the catalyst made with the organotemplate-free zeolite beta synthesized without the use of an organic structure directing agent provided a significantly higher cumene selectivity versus catalysts made with zeolite beta synthesized using conventional organic structure directing agents. In addition to the lower quantities of di-isopropylbenzenes, the quantity of unselective products (which includes oligomers and other products that cannot be converted to cumene) is significantly lower for Catalyst B compared to Catalyst A.

Comparisons of the cumene selectivity provided by Catalyst A at various reaction temperatures against the cumene selectivity provided by Catalyst B at the same reaction temperatures indicate significant differences. The inventive process for preparing cumene uses the organotemplate-free zeolite beta that provides for a significantly higher cumene selectivity than the conventionally prepared zeolite beta (i.e., zeolite beta prepared with the use of an organotemplate) at each of the reaction temperatures. This improved cumene selectivity provides for a number of benefits associated with the inventive cumene preparation process. The higher cumene selectivity allows for lower reaction temperatures which provide for lower energy requirements. Also, it provides for lower distillation requirements and less recycle that provide for additional reductions in energy requirements.

Table 2 presents the test results from using Catalyst A and Catalyst B in benzene alkylation to yield cumene at three different reaction weight hourly space velocities (WHSV). In these experiments, each catalyst was tested for its performance in the propylene alkylation of benzene. A feedstock had a benzene-to-propylene molar ratio of 7 and was passed over the catalyst within a reactor maintained at a temperature of 130° C. The feed rate was set so as to provide each of the indicated weighted hourly space velocities. The reaction pressure was 300 psig (21.7 bar).

The data presented in Table 2 show that for all WHSVs tested Catalyst B provides a higher cumene selectivity. The data also show that for the range of WHSV tested Catalyst B exhibited little sensitivity in its cumene selectivity to changes in the WHSV. The cumene selectivity of the catalyst did not materially change over the range of WHSV tested.

TABLE 1

Presentation of the test results of the use of various zeolite beta catalysts in the preparation of cumene by the alkylation of benzene with propylene at different reaction temperatures.

| Catalyst | Reaction Temperature (°C./° F.) | Propylene conversion | Cumene Selectivity | 1,3 DIPB | 1,4 DIPB | Total Unselective products |
|---|---|---|---|---|---|---|
| Catalyst A | 130/266 | 99.8 | 94.07 | 2.54 | 2.55 | 0.85 |
| | 145/293 | 99.8 | 94.34 | 2.47 | 2.44 | 0.75 |
| | 160/320 | 99.8 | 94.12 | 2.73 | 2.20 | 0.95 |
| Catalyst B | 130/266 | 99.8 | 96.33 | 1.81 | 1.86 | 0.00 |
| | 145/293 | 99.8 | 96.00 | 1.90 | 1.92 | 0.19 |
| | 160/320 | 99.8 | 95.56 | 2.27 | 1.84 | 0.33 |

TABLE 2

Presentation of the test results of the use of various zeolite beta catalysts in the preparation of cumene by the alkylation of benzene with propylene at different reaction space velocities.

| Catalyst | Reaction WHSV ($hr^{-1}$) | Propylene WHSV ($hr^{-1}$) | Propylene conversion | Cumene Selectivity | 1,3 DIPB | 1,4 DIPB | Total Unselective products |
|---|---|---|---|---|---|---|---|
| Catalyst A | 6.0 | 0.42 | 99.8 | 92.92 | 3.56 | 2.98 | 0.54 |
| | 12.0 | 0.86 | 99.9 | 93.13 | 3.49 | 2.94 | 0.45 |
| | 18.0 | 1.29 | 99.9 | 93.32 | 3.41 | 2.90 | 0.37 |
| Catalyst B | 6.0 | 0.42 | 99.9 | 94.39 | 3.36 | 2.24 | 0.08 |
| | 12.0 | 0.86 | 99.9 | 94.31 | 3.36 | 2.24 | 0.09 |
| | 18.0 | 1.29 | 99.9 | 94.40 | 3.29 | 2.24 | 0.46 |

Table 3 presents the test results from using Catalyst A and Catalyst B in benzene alkylation to yield cumene for feed compositions having s benzene-to-propylene (B/P) molar ratio of either 7 or 4. In these tests, each catalyst was tested for its performance in the propylene alkylation of benzene. A feedstock having a B/P molar ratio of either 4 or 7 was passed over the catalyst within a reactor maintained at a temperature of 130° C. and a reaction pressure of 300 psig (21.7 bar). The data presented in Table 4 show that, for a given B/P molar ratio in the feed, Catalyst B provides a higher cumene selectivity. The data also show that cumene selectivity increases with increases in the B/P ratio. The use of the organotemplate-free zeolite beta in the inventive process allows for the use of process feeds that have a lower B/P molar ratios but still achieve higher cumene selectivities. This provides for lower benzene recycle rates and lower energy use. This benefit further allows for the design of smaller process equipment resulting in lower capital cost.

TABLE 3

Presentation of the test results of the use of various zeolite beta catalysts in the preparation of cumene by the alkylation of benzene with propylene at different reaction mixture benzene-to-propylene molar ratios.

| Catalyst | Reaction Mixture Benzene to Propylene Molar Ratio (B/P) | Propylene conversion | Cumene Selectivity | 1,3 DIPB | 1,4 DIPB | Total Unselective products |
|---|---|---|---|---|---|---|
| Catalyst A | 7.0 | 99.8 | 92.9 | 3.56 | 2.98 | 0.54 |
|  | 4.0 | 99.9 | 88.9 | 4.64 | 3.92 | 2.50 |
| Catalyst B | 7.0 | 99.9 | 94.5 | 3.41 | 3.56 | 0.16 |
|  | 4.0 | 99.9 | 90.3 | 5.31 | 4.64 | 1.30 |

The invention claimed is:

1. A process for preparing cumene by alkylation of benzene with propylene, wherein said process comprises:
    contacting a feed mixture, comprising benzene and propylene, at a reactor inlet temperature from 80 to 130 ° C. and an WHSV from 6 to 20, with a benzene alkylation catalyst contained within a reaction zone defined by a reactor, wherein said benzene alkylation catalyst comprises an organotemplate-free zeolite beta, having a silica-to-alumina molar ratio (SAR) of less than 20, that is synthesized in the presence of a material absence of an organotemplate; and
    yielding an alkylation product, comprising cumene;
    wherein said process provides for a high cumene selectivity of at least 94%.

2. A process as recited in claim 1, wherein said organotemplate-free zeolite beta comprises no more than an impurity of an organic structure directing agent.

3. A process as recited in claim 2, wherein said benzene alkylation catalyst has a material absence of a metal component of either iron or copper, or both.

4. A process as recited in claim 3, wherein mild benzene alkylation reaction conditions include a reaction temperature and a reaction pressure such that said feed mixture is at least partially in a liquid phase.

5. A process as recited in claim 4, wherein said feed mixture has a benzene-to-propylene molar ratio of less than 8:1.

6. A process as recited in claim 1, wherein said process provides for a propylene conversion of at least 99.7% with a low selectivity to polyisopropylbenzene of less than 6%.

7. A process as recited in claim 6, wherein said organotemplate-free zeolite beta is made by crystallizing under crystallization conditions a mixture:
    comprising, no more than an impurity of an organic structure directing agent, a solvent comprising water, a source of $Al_2O_3$, a source of $SiO_2$, and a source of hydroxide anions $OH^-$ selected from either sodium hydroxide or potassium hydroxide, wherein the components of said mixture are present in relative amounts so as to provide said mixture having the following molar composition: $xSiO_2·yAl_2O_3:z\ Na_2O:wH_2O$; wherein x =1 to 40; y=1; z=0.1 to 10; w=50 to 1,000; and wherein said mixture further includes zeolite beta seed crystals in an amount in the range of from 0.1 wt. % to 50 wt. % of the total weight of said mixture.

8. A process as recited in claim 7, wherein said organotemplate-free zeolite beta has a material absence of a metal component of either iron or copper, or both.

9. A process for preparing cumene by alkylation of benzene with propylene, wherein said process comprises:
    contacting a feed mixture, comprising benzene and propylene in relative proportions such that the molar ratio of benzene-to-propylene is less than 12:1, at a reactor inlet temperature from 80 to 130 ° C. and an WHSV from 6 to 20with a benzene alkylation catalyst contained within a reaction zone defined by a reactor, wherein said benzene alkylation catalyst comprises an organotemplate-free zeolite beta, having a silica-to-alumina molar ratio (SAR) of less than 20, that is synthesized in the presence of a material absence of an organotemplate; and
    yielding an alkylation product, comprising benzene, cumene, and at least one other reaction product;
    wherein the process provides for a high cumene selectivity of at least 94%.

10. A process as recited in claim 9, wherein said at least one other reaction product includes poly alkylated benzenes and said alkylation product further comprises propane, and said process further comprises: separating propane from said alkylation product to yield a propane product stream, a benzene product stream, and a poly alkylated benzene product stream.

11. A process as recited in claim 10, wherein said process further comprises: mixing a portion of said benzene product stream with said feed mixture.

12. A process as recited in claim 11, wherein said poly alkylated benzene product stream includes diisopropylbenzene and heavy hydrocarbons and said process further comprises: separating diisopropylbenzene from said poly alkylated benzene product stream to yield a diisopropylbenzene product stream and a heavy hydrocarbon stream.

13. A process as recited in claim 12, further comprising: contacting said diisopropylbenzene product stream under transalkylation reaction conditions with a transalkylation catalyst to yield a transalkylation reaction product and including a portion of said transalkylation reaction product with said alkylation product.

14. A process as recited in claim 13, wherein mild benzene alkylation reaction conditions include a reaction pressure such that said feed mixture is at least partially in a liquid phase, and the benzene-to-propylene molar ratio of said feed mixture of less than 8.

15. A process as recited in claim 14, wherein said process provides for a propylene conversion of at least 99.7% with a low selectivity to polyisopropylbenzene of less than 6%.

16. A process as recited in claim 15, wherein said organotemplate-free zeolite beta comprises no more than an impurity of an organic structure directing agent.

17. A process as recited in claim 16, wherein said benzene alkylation catalyst further comprises an inorganic oxide component present in said benzene alkylation catalyst in the range of from 5 wt. % to 50 wt. % of the benzene alkylation catalyst and said organotemplate-free zeolite beta is present in said benzene alkylation catalyst in the range of from 50 wt. % to 95 wt. % of the benzene alkylation catalyst.

18. A process as recited in claim 17, wherein said organotemplate-free zeolite beta is made by crystallizing under crystallization conditions a mixture: comprising, no more than an impurity of an organic structure directing agent, a solvent comprising water, a source of $Al_2O_3$, a source of $SiO_2$, and a source of hydroxide anions $OH^-$ selected from either sodium hydroxide or potassium hydroxide, wherein the components of said mixture are present in relative amounts so as to provide said mixture having the following molar composition: $xSiO_2$:$yAl_2O_3$:$z\ Na_2O$:$wH_2O$; wherein x =1 to 40; y=1; z=0.1 to 10; w=50 to 1,000; and wherein said mixture further includes zeolite beta seed crystals in an amount in the range of from 0.1 wt. % to 50 wt. % of the total weight of said mixture.

19. A process as recited in claim 18, wherein said organotemplate-free zeolite beta has a material absence of a metal component of either iron or copper, or both.

* * * * *